United States Patent
Hebrank et al.

(10) Patent No.: US 7,573,566 B2
(45) Date of Patent: Aug. 11, 2009

(54) METHODS AND APPARATUS FOR MAINTAINING EFFECTIVE OPERATION OF APPARATUS FOR CANDLING AVIAN EGGS

(75) Inventors: John H. Hebrank, Durham, NC (US); Thomas Bryan, Raleigh, NC (US)

(73) Assignee: Embrex, Inc., Durham, NC (US)

( * ) Notice: Subject to any disclaimer, the term of this patent is extended or adjusted under 35 U.S.C. 154(b) by 0 days.

(21) Appl. No.: 11/487,614

(22) Filed: Jul. 17, 2006

(65) Prior Publication Data

US 2007/0024843 A1    Feb. 1, 2007

Related U.S. Application Data

(60) Provisional application No. 60/703,044, filed on Jul. 27, 2005.

(51) Int. Cl.
*A01K 43/00* (2006.01)
*G01N 33/08* (2006.01)

(52) U.S. Cl. .......................... 356/53; 356/52

(58) Field of Classification Search ....................... None
See application file for complete search history.

(56) References Cited

U.S. PATENT DOCUMENTS

| | | | |
|---|---|---|---|
| 2,044,981 A * | 6/1936 | Guttman | 209/511 |
| 2,403,705 A * | 7/1946 | Bramson | 356/59 |
| 4,458,630 A | 7/1984 | Sharma et al. | |
| 4,681,063 A | 7/1987 | Hebrank | |
| 4,914,672 A | 4/1990 | Hebrank | |
| 4,955,728 A | 9/1990 | Hebrank | |
| 4,978,225 A * | 12/1990 | Reimer | 356/432 |
| 5,028,421 A | 7/1991 | Fredericksen et al. | |
| 5,158,038 A | 10/1992 | Sheeks et al. | |
| 5,745,228 A | 4/1998 | Hebrank et al. | |
| 6,373,560 B1 * | 4/2002 | Roux | 356/58 |
| 6,427,844 B2 * | 8/2002 | Hebrank | 209/510 |

* cited by examiner

*Primary Examiner*—Gregory J Toatley, Jr.
*Assistant Examiner*—Gordon J Stock, Jr.
(74) *Attorney, Agent, or Firm*—Martha G. Munchhof; Gregg C. Benson

(57) ABSTRACT

Egg candling methods and apparatus are provided wherein the optical path between a light source and light detector is monitored for obscuring debris and/or malfunctions. A method of candling eggs includes illuminating an egg with light from a light source; receiving light passing through the egg at a light detector; generating an output signal that corresponds to light received at the light detector for the egg; and analyzing the output signal to determine whether the optical path between the light source and light detector has been altered. In response to determining that a respective optical path has been altered, the light source and/or light detector is cleaned and/or inspected for malfunctions. Cleaning the light source and/or light detector may include wiping a surface of the light source and/or light detector and/or spraying a surface of the light source and/or light detector with a fluid.

8 Claims, 7 Drawing Sheets

US 7,573,566 B2

METHODS AND APPARATUS FOR MAINTAINING EFFECTIVE OPERATION OF APPARATUS FOR CANDLING AVIAN EGGS

RELATED APPLICATION

This application claims the benefit of and priority to U.S. Provisional Patent Application No. 60/703,044, filed Jul. 27, 2005, the disclosure of which is incorporated herein by reference as if set forth in its entirety.

FIELD OF THE INVENTION

The present invention relates generally to eggs and, more particularly, to methods and apparatus for processing eggs.

BACKGROUND OF THE INVENTION

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear, rotted, and dead eggs (collectively referred to as "non-live eggs"). Non-live eggs are typically removed from incubation to increase available incubator space. In many instances it is desirable to introduce a substance, via in ovo injection, into a live egg prior to hatch. Injections of various substances into avian eggs are typically employed in the commercial poultry industry to decrease post-hatch mortality rates or increase growth rates of hatched birds. Examples of substances that have been used for, or proposed for, in ovo injection include vaccines, antibiotics and vitamins. In ovo treatment substances and methods of in ovo injection are described, for example, in U.S. Pat. No. 4,458,630 to Sharma et al. and U.S. Pat. No. 5,028,421 to Fredericksen et al.

In ovo injections of substances typically occur by piercing an egg shell to create a hole therethrough (e.g., using a punch or drill), extending an injection needle through the hole and into the interior of the egg (and in some cases into the avian embryo contained therein), and injecting one or more treatment substances through the needle. An example of an in ovo injection device is disclosed in U.S. Pat. No. 4,681,063 to Hebrank. This device positions an egg and an injection needle in a fixed relationship to each other, and is designed for high-speed automated injection of a plurality of eggs. The selection of both the site and time of injection treatment can impact the effectiveness of the injected substance, as well as the mortality rate of the injected eggs or treated embryos. See, for example, U.S. Pat. No. 4,458,630 to Sharma et al., U.S. Pat. No. 4,681,063 to Hebrank, and U.S. Pat. No. 5,158,038 to Sheeks et al.

In commercial poultry production, typically only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the increasing use of automated methods for in ovo injection, and the cost of treatment substances, an automated method for accurately identifying live eggs and selectively injecting only live eggs, is desirable.

There are other applications where it is important to be able to identify live and non-live eggs. One of these applications is the cultivation and harvesting of vaccines in live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the amniotic fluid from the egg. Typically, eggs are candled before injection of a seed virus to facilitate removal of non-live eggs. Vaccine production eggs may be candled one or more days prior to injection of a seed virus therein. Identification of live eggs in vaccine production is important because it is desirable to prevent seed vaccine from being wasted in non-live eggs and to reduce costs associated with transporting and disposing of non-live eggs.

U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 5,745,228 to Hebrank et al. describes a candling apparatus that includes a photodetector and a photoemitter that are configured to be positioned on opposite sides of an egg. Light is generated in short bursts from each photoemitter and the corresponding photodetector monitors while it's corresponding photoemitter is operational. A flat of eggs is continuously "scanned" as it moves through the candling apparatus with each detector-source pair active while at least adjacent, and preferably all other, pairs are quiescent.

Unfortunately, commercial egg candling devices that utilize light (or egg opacity) to evaluate the condition of an egg usually operate in a dirty environment that can reduce the accuracy of such devices as the optical path is altered by debris and/or other materials that accumulate on the optical surfaces. Operators of machines using these candling devices may not have the training or motivation to keep these devices clean, and/or may not be able to easily access these devices to clean them. For example, a candling apparatus having a light source above moving flats of eggs and light detectors below the moving flats of eggs can have the detectors obscured by a fine layer of egg shell, chunks of egg shell, egg albumin, yoke or rotten innards, wash water, etc. Small accumulations of debris/material typically have a limited effect on the accuracy of an egg candling device. However, opaque materials like chunks of shell or rotten egg materials can reduce received light so that clear eggs may be interpreted by a candling apparatus as live eggs. Furthermore, accumulations of transparent materials, like albumin or water can act as a lens that conducts light reflected off adjacent eggs into the detector so that live eggs can be misinterpreted as being clear eggs. Exploding eggs, that are not uncommon, can spray both light detectors and light sources.

SUMMARY OF THE INVENTION

In view of the above discussion, egg candling methods and apparatus are provided wherein the optical path between a light source and light detector is monitored for obscuring debris and/or equipment malfunctions. According to some embodiments of the present invention, a method of candling eggs includes illuminating an egg with light from a light source; receiving light passing through the egg at a light detector; generating an output signal that corresponds to light received at the light detector for the egg; and analyzing the output signal to determine whether the optical path between the light source and light detector has been altered (i.e., the optical bath has been blocked or partially blocked by debris/material, the light source and/or light detector malfunctioned, etc.). In response to determining that a respective optical path has been altered, the light source and/or light detector is cleaned and/or inspected for malfunctions. According to some embodiments of the present invention, cleaning the light source and/or light detector may include wiping a surface of the light source and/or light detector and/or spraying a surface of the light source and/or light detector with a fluid (e.g., a cleaning fluid, water, air, etc.).

According to some embodiments of the present invention, a candling apparatus includes a plurality of pairs of light sources and light detectors in spaced apart relationship such that a carrier of eggs may pass therebetween. Each light source/light detector pair is operatively associated with a processor, and each light source/light detector pair defines a respective optical channel. In some embodiments of the present invention the light sources will be below the eggs and the light detectors above, and in other embodiments the light detectors will be below the eggs and the light sources above the eggs.

A method of candling eggs via the candling apparatus includes illuminating eggs in a carrier with light from the light sources, wherein the eggs are arranged in rows and columns within the carrier, and wherein each egg in a row is positioned between a respective light source/light detector pair; receiving light passing through each egg at a corresponding light detector; generating an output signal that corresponds to light received at a light detector for each respective egg; and analyzing the output signals of each optical channel to determine whether the optical path between any of the light source/light detector pairs has been altered. In response to determining that a respective optical path has been altered, the light source and/or light detector is cleaned and/or inspected for malfunctions. According to some embodiments of the present invention, cleaning the light source and/or light detector may include wiping a surface of the light source and/or light detector and/or spraying a surface of the light source and/or light detector with a fluid (e.g., a cleaning fluid, water, air, etc.).

According to some embodiments of the present invention, analyzing the output signals of each optical channel to determine whether the optical path between any of the light source/light detector pairs has been altered includes detecting whether an average opacity value of clear eggs candled via an optical channel has dropped below an average opacity value of clear eggs candled via the other optical channels.

According to some embodiments of the present invention, analyzing the output signals of each optical channel to determine whether the optical path between any of the light source/light detector pairs has been altered includes detecting a drop in frequency of occurrence of clear eggs.

According to some embodiments of the present invention, analyzing the output signals of each optical channel to determine whether the optical path between any of the light source/light detector pairs has been altered includes detecting an increase in average light level of live eggs in an optical channel relative to historical values for that channel.

According to some embodiments of the present invention, analyzing the output signals of each optical channel to determine whether the optical path between any of the light source/light detector pairs has been altered comprises detecting an increase in average light level of live eggs in an optical channel relative to historical values for other optical channels.

According to some embodiments of the present invention, analyzing the output signals of each optical channel to determine whether the optical path between any of the light source/light detector pairs has been altered comprises detecting a reduction in light levels received at a light detector in an optical channel relative to historical light levels for the optical channel.

According to some embodiments of the present invention, an apparatus for candling eggs includes a light source configured to illuminate an egg with light from one or more selected portions of the spectrum; a light detector that receives light passing through an egg and that generates an output signal that corresponds to light received at the light detector for the egg; and a processor in communication with the light detector that analyzes the output signal to determine whether an optical path between the light source and light detector has been altered.

According to some embodiments of the present invention, the candling apparatus includes a wiper that is operatively controlled by the processor and that is configured to wipe a surface of the light source and/or light detector and remove debris/material therefrom.

According to some embodiments of the present invention, the candling apparatus includes a cleaning fluid application system that is operatively controlled by the processor and that is configured to spray a surface of the light source and/or light detector with a fluid (e.g., a cleaning fluid, water, air, etc.).

According to some embodiments of the present invention, the candling apparatus includes a sheet of transparent material positioned adjacent to the light source that prevents debris from altering the optical path between the light source and light detector. The transparent material moves relative to the light source and is configured to carry away debris in contact therewith.

According to some embodiments of the present invention, the candling apparatus includes a sheet of transparent material positioned adjacent to the light detector that prevents debris from altering the optical path between the light source and light detector. The transparent material moves relative to the light detector and is configured to carry away debris in contact therewith.

According to some embodiments of the present invention, the processor is configured to detect whether an average opacity value of clear eggs candled via an optical channel has dropped below an average opacity value of clear eggs candled via the other optical channels.

According to some embodiments of the present invention, the processor is configured to detect a drop in frequency of occurrence of clear eggs.

According to some embodiments of the present invention, the processor is configured to detect an increase in average light level of live eggs.

According to some embodiments of the present invention, the processor is configured to detect a reduction in light levels relative to historical light levels.

According to some embodiments of the present invention, an apparatus for candling eggs includes a plurality of pairs of light sources and light detectors in spaced apart relationship such that eggs may pass therebetween, wherein each light source is configured to illuminate an egg with light from one or more selected portions of the spectrum, wherein each light detector is configured to receive light passing through an egg and to generate an output signal that corresponds to light received at the light detector for the egg, and wherein each light source/light detector pair defines a respective optical channel; and a processor in communication with each optical channel that analyzes the output signals of each optical channel to determine whether an optical path between a light source and respective light detector has been altered.

According to some embodiments of the present invention, the processor is configured to detect whether an average opacity value of clear eggs candled via an optical channel has dropped below an average opacity value of clear eggs candled via the other optical channels.

According to some embodiments of the present invention, the processor is configured to detect a drop in frequency of occurrence of clear eggs.

According to some embodiments of the present invention, the processor is configured to detect an increase in average light level of live eggs in an optical channel relative to historical values for that channel.

According to some embodiments of the present invention, the processor is configured to detect an increase in average light level of live eggs in an optical channel relative to historical values for other optical channels.

According to some embodiments of the present invention, the processor is configured to detect a reduction in light levels received at a light detector in an optical channel relative to historical light levels for the optical channel.

According to some embodiments of the present invention, the candling apparatus includes a wiper that is operatively controlled by the processor and that is configured to wipe a surface of the light source and/or light detector and remove debris/material therefrom.

According to some embodiments of the present invention, the candling apparatus includes a cleaning fluid application system that is operatively controlled by the processor and that is configured to spray a surface of the light source and/or light detector with a fluid (e.g., a cleaning fluid, water, air, etc.).

According to some embodiments of the present invention, the candling apparatus includes a sheet of transparent material positioned adjacent to the light source that prevents debris from altering the optical path between the light source and light detector. The transparent material moves relative to the light source and is configured to carry away debris in contact therewith.

According to some embodiments of the present invention, the candling apparatus includes a sheet of transparent material positioned adjacent to the light detector that prevents debris from altering the optical path between the light source and light detector. The transparent material moves relative to the light detector and is configured to carry away debris in contact therewith.

DETAILED DESCRIPTION OF THE INVENTION

Figure 1:
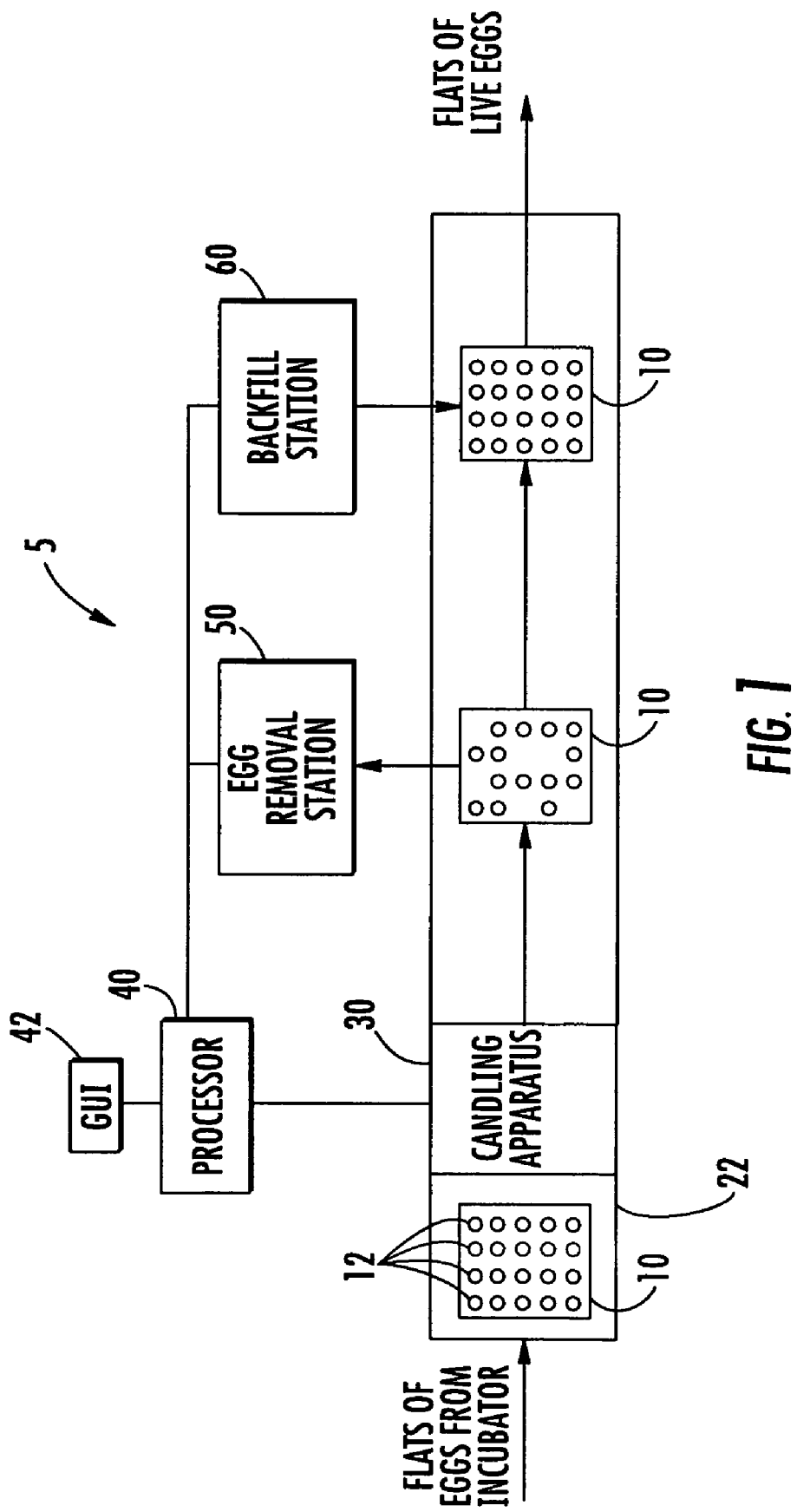
FIG. 1 is a block diagram of an egg processing system having an egg candling apparatus, according to some embodiments of the present invention.

The present invention now is described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. All publications, patent applications, patents, and other references mentioned herein are incorporated herein by reference in their entireties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

FIG. 1 is a block diagram of an egg processing system 5 having an egg candling apparatus 30 that is configured to identify live eggs, according to embodiments of the present invention. A carrier (e.g., an egg flat) 10 of eggs 12 is conveyed via a conveyor 22 to the candling apparatus 30 that is configured to designate each egg 12 within the flat 10 as being either live or non-live. Any type of conveying system suitable for conveying flats of eggs may be utilized in accordance with embodiments of the present invention. Egg conveying systems are well known to those of skill in the art and need not be described further herein.

Although eggs conventionally are carried in egg flats, any means of presenting a plurality of eggs over time to a candling station 30, as well as to other egg processing equipment, may be used. Egg flats of virtually any type may be used in accordance with embodiments of the present invention. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein.

The candling apparatus 30 includes a plurality of light sources that illuminate eggs within a carrier with light and a plurality of corresponding light detectors that receive light passing through the eggs from the light sources and that generate an output signal that corresponds to received light, as will be described below. An exemplary light candling apparatus that may be utilized in accordance with some embodiments of the present invention is described in, for example, U.S. Pat. No. 5,745,228 to Hebrank et al. A suitable commercial light candling system that may be utilized in accordance with some embodiments of the present invention includes, for example, the S Beam light candling system of the Egg Remover® candling system available from Embrex, Inc. of Research Triangle Park, N.C.

The illustrated candling apparatus 30 is operatively connected to a processor 40 which controls operations of the candling apparatus 30, analyzes the output signal from each light detector and stores information received from the candling apparatus 30 about each egg 12. An operator interface (e.g., a display) 42 may be provided to allow an operator to interact with the processor 40. The processor 40 may control various other downstream egg processing operations, as well, including, for example, an egg removal station 50 and backfill station 60.

In the illustrated apparatus, eggs 12 designated as non-live are removed from the flat 10 downstream from the candling apparatus 30 at egg removal station 50. The processor 40 generates a selective removal signal for eggs determined to be non-live by the candling apparatus 30. The non-live eggs are removed from the flat 10 and discarded or used for some other purpose.

Figure 2:
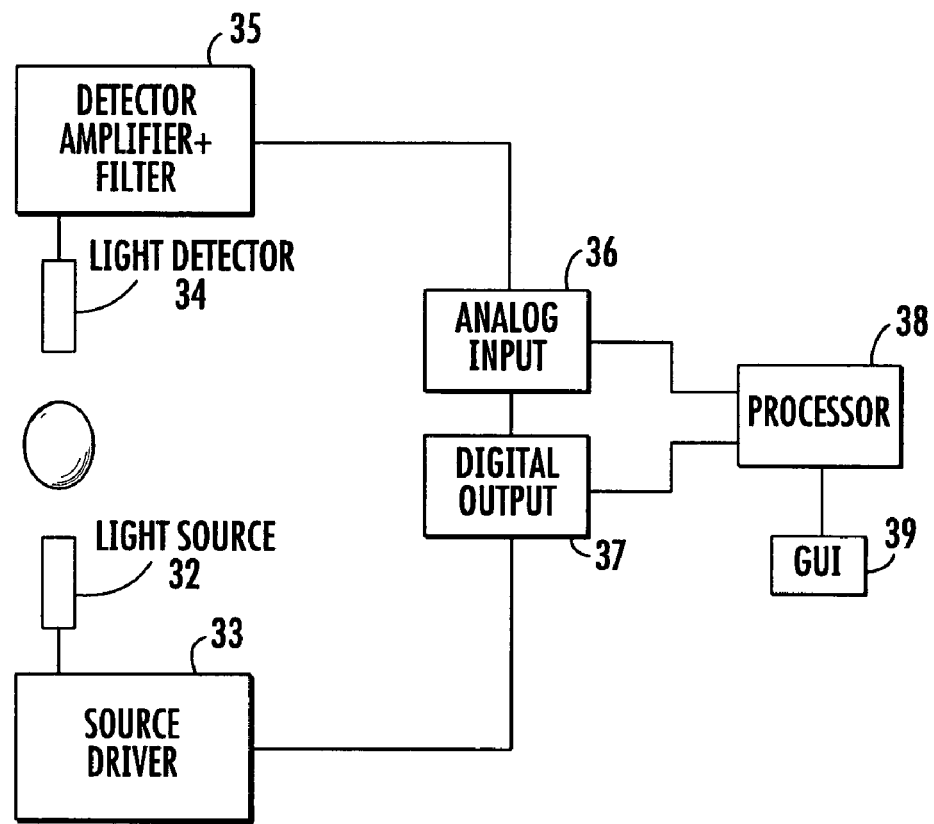
FIG. 2 is a block diagram of a light source and light detector pair from the candling apparatus of FIG. 1.

FIG. 2 illustrates an exemplary light source 32 and light detector 34 pair from the candling apparatus 30 of FIG. 1. The candling apparatus 30 contains a plurality of light source/light detector pairs to correspond with a row of eggs in a carrier, such as an egg flat. Each light source/light detector pair defines a respective optical channel. Each light detector 34 is associated with a detector amplifier and filter circuit 35, which is in turn associated with an analog input board 36. Each light source 32 (e.g., an infrared light source, etc.) is associated with a light source driver circuit 33, which is in turn associated with a digital output board 37. The light source 32 and light detector 34 in each pair are positioned on opposite sides of an egg, as would be understood by those skilled in the art. In FIG. 2, the light detector 34 is above and the light source 32 is below the egg, but these positions are not critical and could be reversed, or the light source and light detector may be placed in different orientations, so long as light from the light source illuminates the egg to the light detector. Embodiments of the present invention are not limited to the illustrated orientation and configuration of the light source 32 and light detector 34.

The input and output boards 36, 37 may physically be one or more separate boards and are associated with a processor 38 (e.g., a personal computer or other computing device), with operation of the system monitored on a user interface 39 associated with the processor. In operation, light is generated in short bursts from each light source 32 (e.g., 50 to 300 microseconds) and the corresponding light detector 34 monitors while its corresponding light source 32 is operational. To reduce the effect of ambient light, the output of a light detector 34 when no light is on is subtracted from the reading when the light is on. A flat of eggs is continuously "scanned" as it moves through the candling apparatus 30 with each light detector/light source pair active while at least adjacent, and preferably all other, light detector/light source pairs are quiescent.

Figure 3:
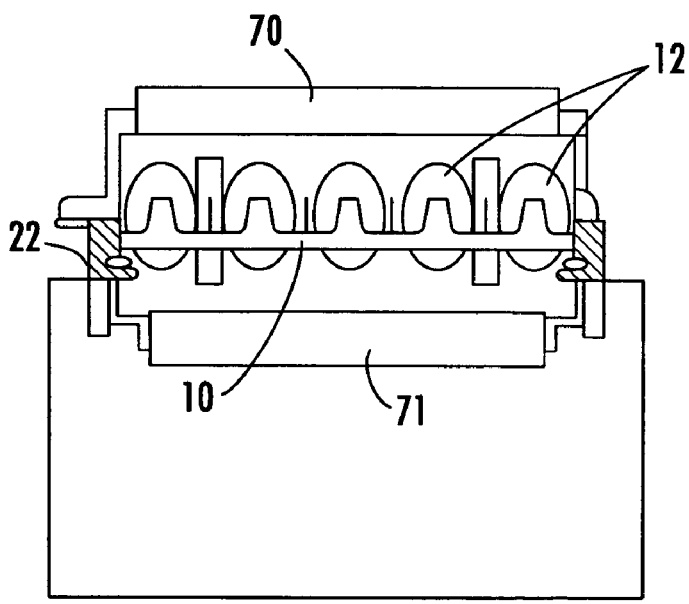
FIG. 3 is an end view of an exemplary candling apparatus illustrating an egg carrier positioned between a light source mounting block containing a plurality of light sources and a light detector mounting block containing a plurality of light detectors, according to some embodiments of the present invention.
Figure 5:
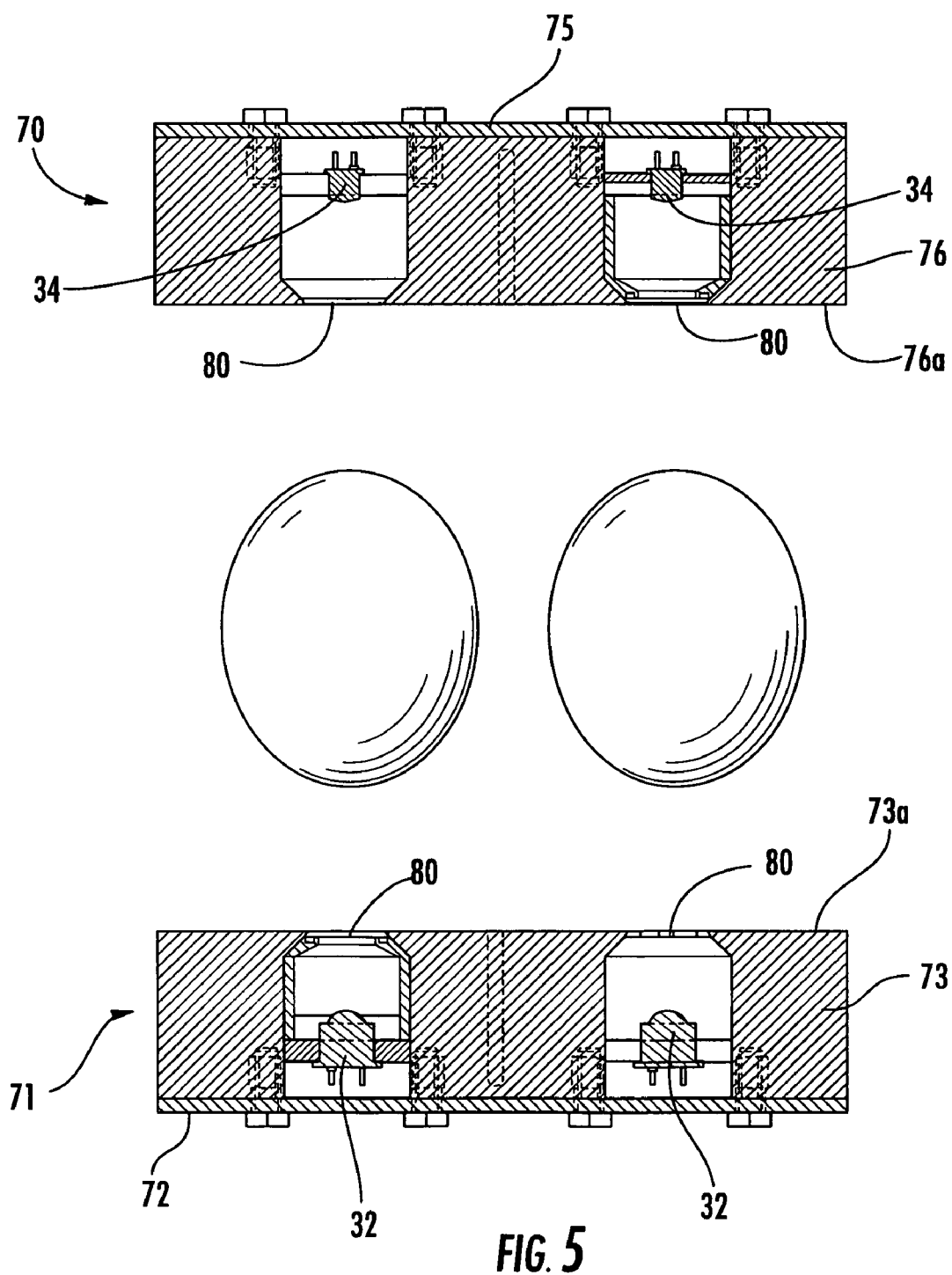
FIG. 5 is a partial enlarged cross-sectional view of the light source and light detector mounting blocks of FIG. 3.

FIG. 3 is an end view of a candling apparatus 30, according to some embodiments of the present invention. The candling apparatus 30 includes a light source mounting block 71 containing a plurality of light sources 32 disposed therewithin in adjacent, spaced-apart relationship (FIG. 5), and a light detector mounting block 70 containing a plurality of light detectors 34 disposed therewithin in adjacent, spaced-apart relationship (FIG. 5). The illustrated candling apparatus 30 also includes a conveyor 22 that transports egg carriers 10 containing eggs 12 between the light source mounting block 71 and the light detector mounting block 70.

FIG. 5 is a partial enlarged cross-sectional view of the light source and light detector mounting blocks 71, 70 of FIG. 3. The illustrated light source mounting block 71 includes an opaque back plate 72 with light sources 32 (e.g., Photonics Detectors, Inc. infrared light sources, Part number PDI-E805, etc.) disposed therewithin. These light sources 32 include an integral lens, but a non-integral lens system may also be provided for each light source. The illustrated light source mounting block 71 also includes an opaque polymer block 73 attached to the back plate 72. The polymer block 73 has apertures bored therethrough in corresponding relation to each light source 32. The light source mounting block 71 also includes sapphire disks 80 disposed within the respective apertures formed in the block 73 so as to be generally flush with the upper surface 73a thereof. Each sapphire disk 80 protects a respective light source 32 by preventing debris (e.g., liquids, etc.) from passing through an aperture and reaching a light source 32. In addition, each sapphire disk 80 provides a generally flat surface that can be cleaned easily and that does not accumulate or pool water and other materials/liquids. Sapphire is sufficiently hard that routine wiping will not scratch the surface and cause light to scatter on to adjacent eggs. However, the disks 80 may be formed from other materials. Embodiments of the present invention are not limited to sapphire disks. The structure of the mounting block 71 thus provides an optical aperture positioned between an egg and a respective light source 32 with a surface (e.g., sapphire disk 80) that prevents debris from damaging the light source 32.

The light detector mounting block 70 has a similar construction. The illustrated light detector mounting block 70 includes an opaque back plate 75 with light detectors 34 (e.g., Texas Instruments infrared detectors, Part number TSL261, etc.) disposed therewithin. Integral lenses or non-integral lens systems could optionally be provided with the light detectors 34. The illustrated light detector mounting block 70 also includes an opaque polymer block 76 attached to the back plate 75. The polymer block 76 has apertures bored therethrough in corresponding relation to each light detector. The light detector mounting block 76 also includes sapphire disks 80 disposed within the respective apertures formed in the block 76 so as to be generally flush with the lower surface 76a thereof. Each sapphire disk 80 protects a respective light detector 34 by preventing debris (e.g., liquids, etc.) from passing through an aperture and reaching a light detector 34. In addition, each sapphire disk 80 provides a generally flat surface that can be cleaned easily and that does not accumulate or pool water and other materials/liquids. As described above, the disks 80 may be formed from other materials. Embodiments of the present invention are not limited to sapphire disks. The structure of the mounting block 76 thus provides an optical aperture positioned between an egg and a respective light detector 34 with a surface (e.g., sapphire disk 80) that prevents debris from damaging the light detector 34.

Blocks 73, 76 may be formed from various materials and are not limited to polymer materials.

Figure 4A:
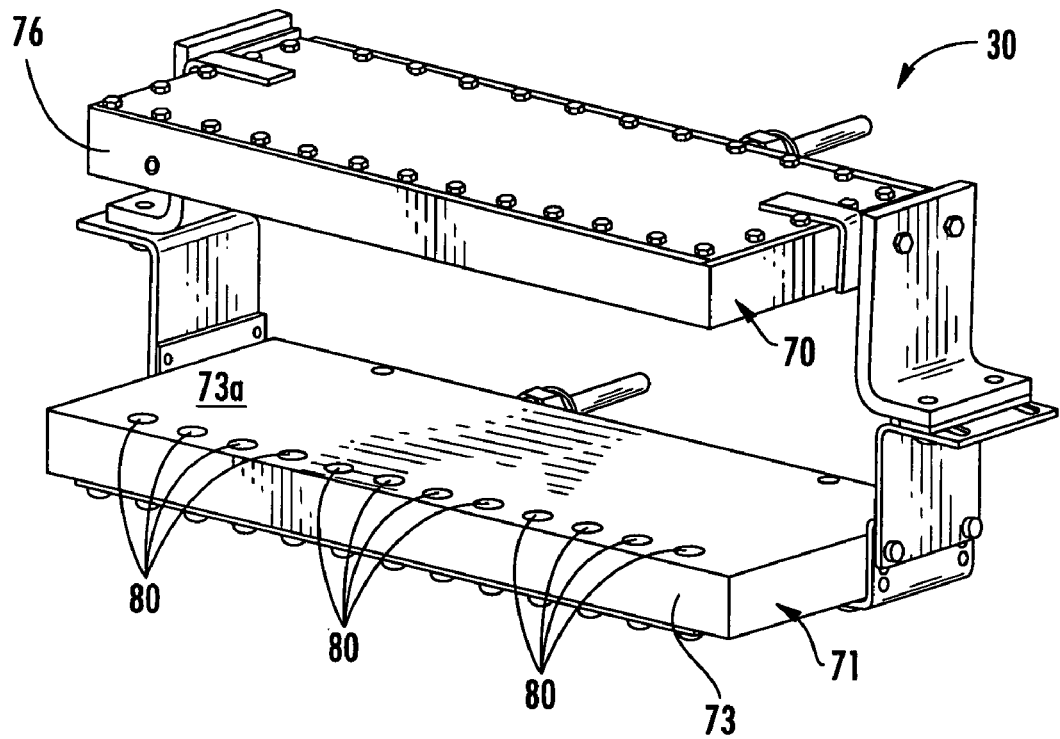
FIG. 4A is a perspective view of the candling apparatus of FIG. 3 that illustrates a plurality of light sources in the light source mounting block.
Figure 4B:
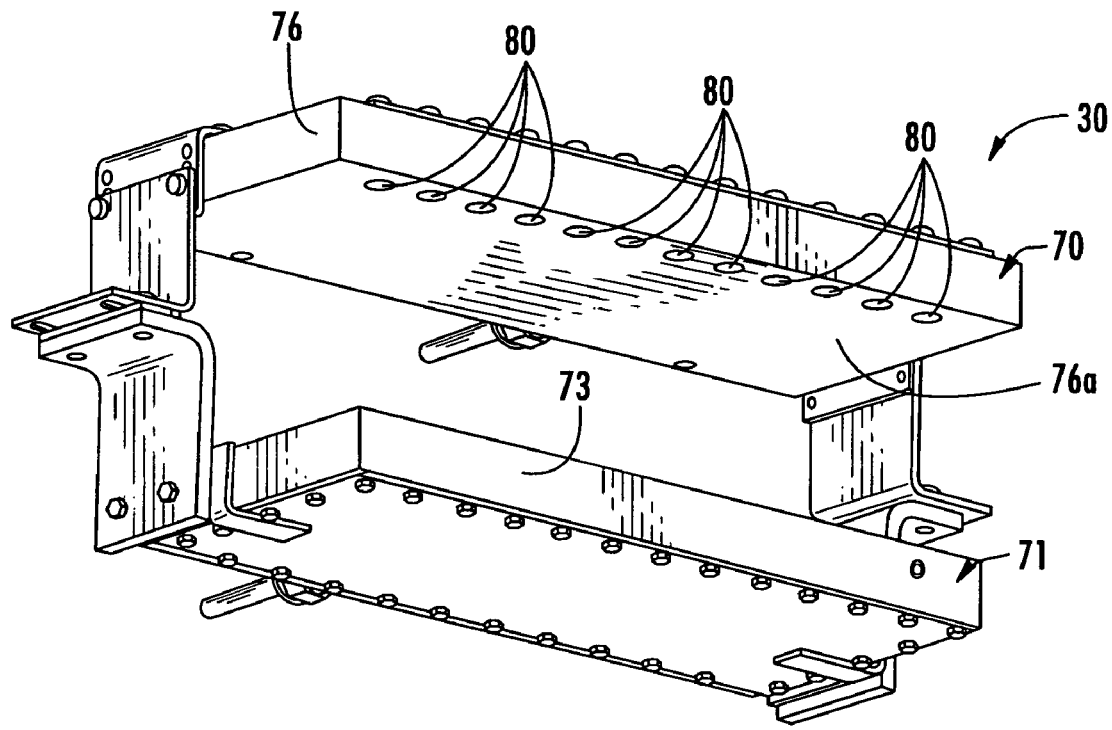
FIG. 4B is a perspective view of the candling apparatus of FIG. 3 that illustrates a plurality of light detectors in the light detector mounting block.

FIG. 4A is a perspective view of the candling apparatus 30 of FIG. 3 illustrating block surface 73a having a plurality of sapphire disks 80 substantially flush therewith. FIG. 4B is a perspective view of the candling apparatus 30 of FIG. 3 illustrating block surface 76a having a plurality of sapphire disks 80 substantially flush therewith.

Embodiments of the present invention are not limited to the illustrated candling apparatus 30. Embodiments of the present invention may be implemented with any candling apparatus, without limitation.

Figure 6:
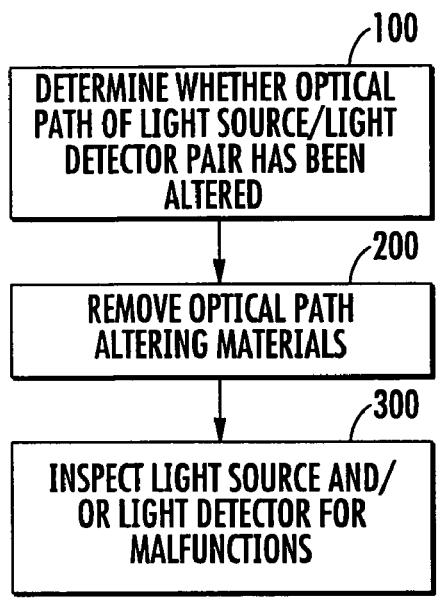
FIGS. 6-8 are flow charts of operations for maintaining effective operation of candling devices, according to some embodiments of the present invention.
Figure 7:
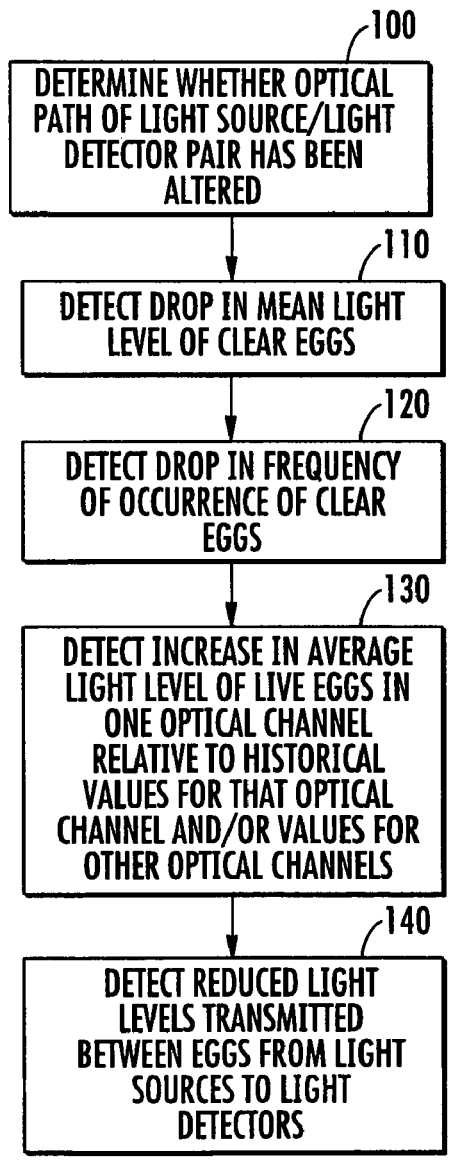
Figure 8:
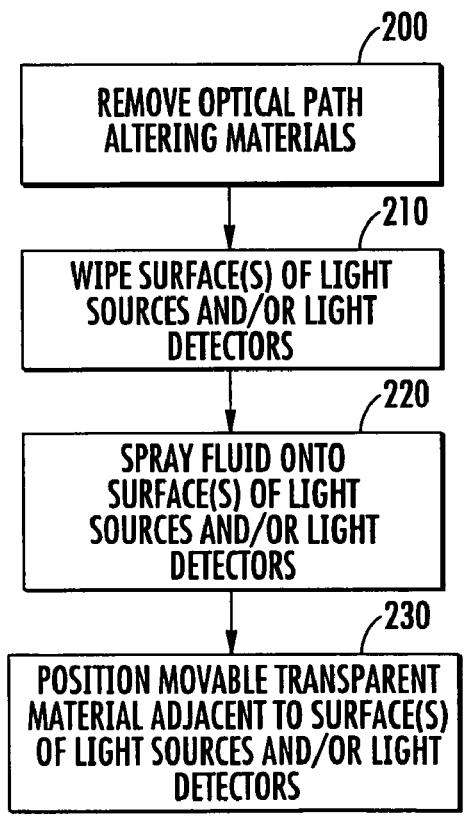

Referring now to FIGS. 6-8, methods of candling eggs that facilitate maintaining effective candling operation, according to embodiments of the present invention, are illustrated. Initially, a determination is made whether the optical path (i.e., the optical path from a light source 32 to a light detector 34) of a candling apparatus has been altered (Block 100). In response to determining that the optical path has been altered, altering materials (e.g., egg debris, water, etc.) is removed from the optical path or neighboring region (Block 200) and/or the light source/light detector pair is inspected for malfunctions (Block 300). Determining whether the optical path of a candling device has been altered can be performed in various ways. For example, an egg is illuminated with light from a light source 32 during candling operations and light passing through the egg is received at a corresponding light detector 34. The light detector 34 generates as output signal that corresponds to the light received at the light detector 34. The output signal is analyzed in one or more various ways to determine if the optical path has been altered by, for example, debris covering the optical path between the light source 32 and/or light detector 34.

Output signal analysis may include, but is not limited to, detecting a drop in the mean light level of clear eggs (e.g., detecting that the average opacity of clear eggs on one channel drops below the average or median of the average of other channels of the candling apparatus) (Block 110); detecting a drop in the frequency of occurrence of clear eggs (e.g., the percent of clear eggs on one channel drops below that of other channels of a candling device) (Block 120); detecting an increase in the average light level of live eggs in one channel relative to historical values for that channel and/or values for other channels of a candling device (Block 130); and detecting reduced light levels transmitted between eggs from the light sources to the light detectors of a candling apparatus (Block 140). In addition, other ways of determining whether the optical path of a candling apparatus light source/light detector pair has been altered, according to some embodiments of the present invention, include time-based, cycle-based or random assumptions that light sources and/or light detectors should be cleaned, and manual observations by an operator of a candling apparatus.

High light values for live eggs, which falsely indicate that a live egg is a clear egg, can happen when water and/or egg material forms on a lens on a light detector or light source, and/or when fog (e.g., condensation, etc.) causes a light detector to gather stray light from light sources or a light source to scatter light to the side. Generally, when a live egg on one optical channel is consistently seen as a clear egg, the light detectors and light sources should be cleaned and/or checked for fogging.

Removing altering materials from the optical path or neighboring region of a candling apparatus can be performed in various ways in accordance with some embodiments of the present invention. For example, the surface(s) of light sources and/or light detectors (and/or the surfaces of protective materials overlying the light sources/light detectors, such as the sapphire disks 80 described above) can be wiped (e.g., automatically or manually) (Block 210); the surface(s) of light sources and/or light detectors (and/or the surfaces of protective materials overlying the light sources/light detectors, such as the sapphire disks 80 described above) can be sprayed with a fluid (e.g., a cleaning fluid, water, air, etc.) (Block 220); and/or a moving transparent film that blocks debris from reaching the surface(s) of light sources and/or light detectors and carries the debris away may be utilized (Block 230). For example, in the illustrated candling apparatus embodiment of FIG. 5, the surfaces 73a, 76a of respective blocks 73, 76 and the sapphire disks 80 may be wiped and/or sprayed with a fluid to remove debris therefrom.

It is understood that the phrase "cleaning a light source and/or light detector", as used herein, means cleaning the surfaces of protective materials overlying the light sources/light detectors, such as the sapphire disks 80 described above, as well as the light sources/light detectors, themselves. The phrase "cleaning a light source and/or light detector", as used herein, also means cleaning surfaces adjacent to the light sources/light detectors.

Figure 9:
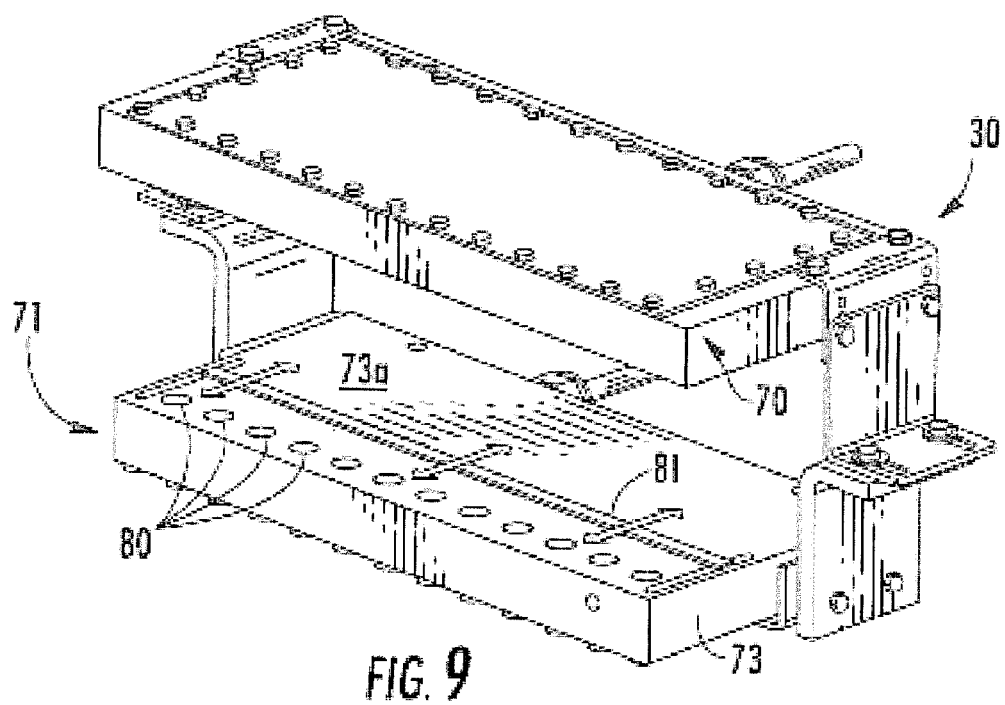
FIG. 9 is a perspective view of the candling apparatus of FIG. 3 having a wiper that is configured to wipe a surface of the light detectors, according to some embodiments of the present invention.

FIG. 9 illustrates the candling apparatus 30 of FIG. 3 with a wiper 81 that is configured to wipe the surface 73a of block 73 and the sapphire disks 80, according to some embodiments of the present invention. A similar wiper may be used to wipe the surface 76a of block 76 housing the light detectors 34. Wiper 81 may have various configurations and may be similar in configuration and operation as a wipe blade for a vehicle windshield.

Figure 10:
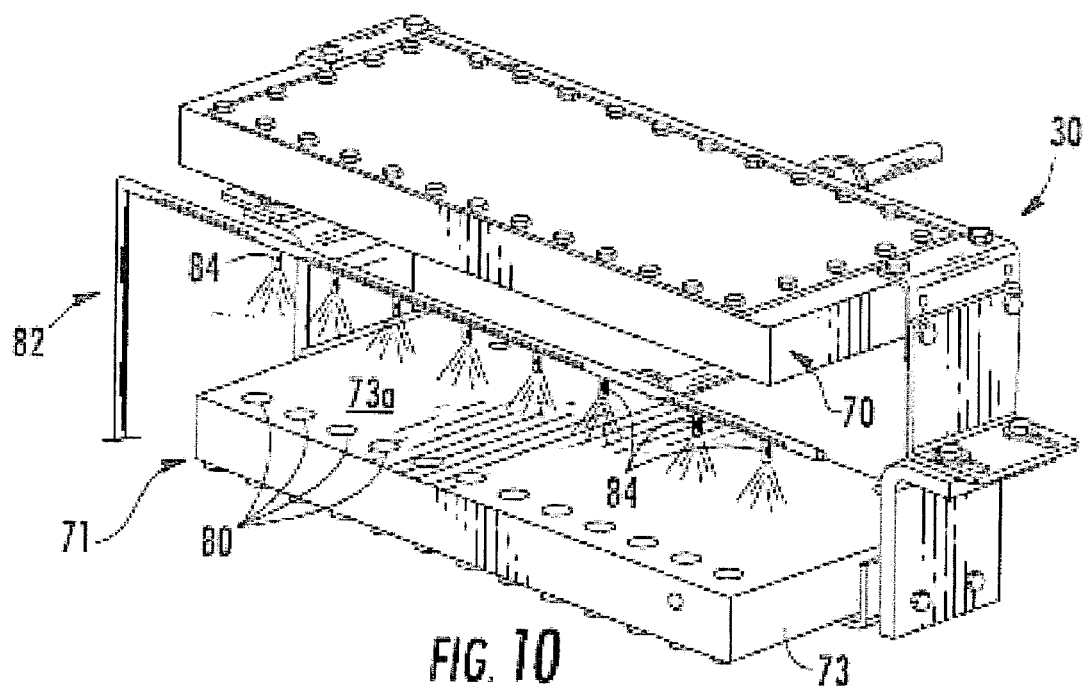
FIG. 10 is a perspective view of the candling apparatus of FIG. 3 having a cleaning fluid application system that is configured to spray a surface of the light detectors with a cleaning fluid, according to some embodiments of the present invention.

FIG. 10 illustrates the candling apparatus 30 of FIG. 3 with a cleaning fluid application system 82 that is configured to spray the surface 73a of the block 73 housing the light sources 32 and the sapphire disks 80 with a cleaning fluid, according to some embodiments of the present invention. In the illustrated embodiment, a series of nozzles 84 are configured to spray fluid (e.g., a cleaning fluid, water, air, etc.) onto the surface 73a and sapphire disks 80. A similar spray system may be used to clean the surface 76a of the block 76 housing the light detectors 34.

Figure 11:
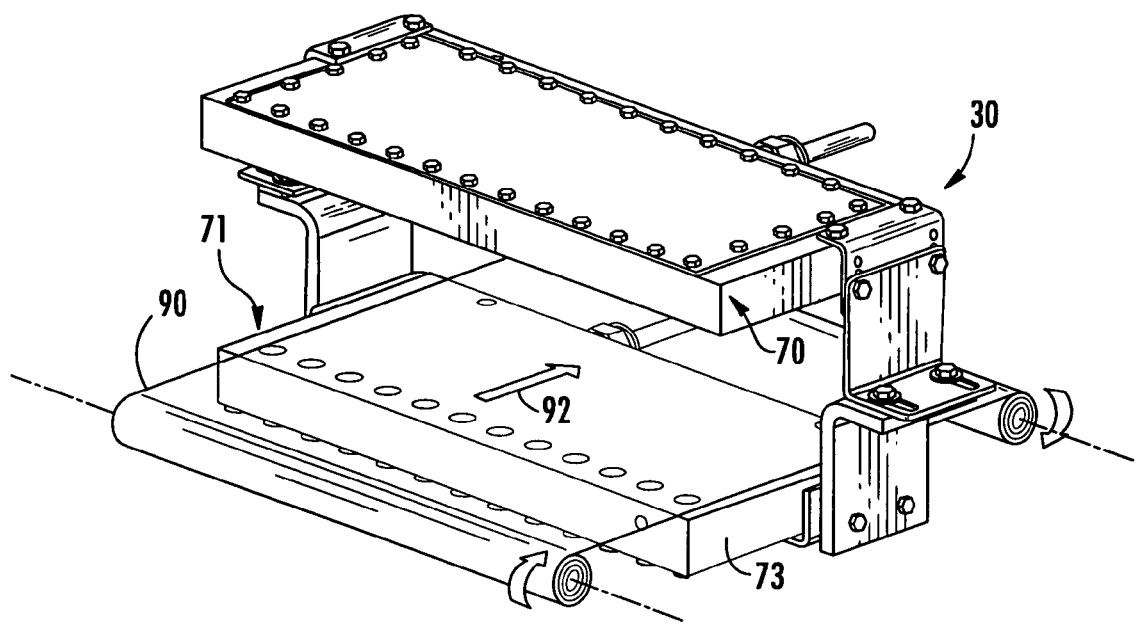
FIG. 11 is a perspective view of the candling apparatus of FIG. 3 having a moving sheet of transparent material positioned adjacent to the light detectors that catches and removes debris away from the light detectors, according to some embodiments of the present invention.

FIG. 11 illustrates the candling apparatus 30 of FIG. 3 with a sheet of transparent material 90 positioned adjacent to the block 73 housing the light detectors 32. The sheet of material 90 is configured to catch debris and periodically move in the direction indicated by arrow 92 to remove the debris away from the light sources 32. A similar system may be used to catch and remove debris from the surface 76a of the block 76 housing the light detectors 34.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. An apparatus for candling eggs, comprising:
    a light source configured to illuminate an egg with light from one or more selected portions of the spectrum,
    a light detector that receives light passing through an egg and that generates an output signal that corresponds to light received at the light detector for the egg; and
    a processor in communication with the photodetector that analyzes the output signal to determine whether an optical path between the light source and the light detector has been altered by debris and/or by a malfunctioning light source or light detector, wherein said apparatus further comprises a wiper operatively controlled by the processor and that is configured to wipe a surface of the light source and/or light detector.

2. The apparatus of claim 1, further comprising a cleaning fluid application system operatively controlled by the processor and that is configured to spray a surface of the light source and/or light detector with a cleaning fluid.

3. The apparatus of claim 2, wherein the processor is configured to detect whether an average opacity value of clear eggs candled via an optical channel has dropped below an average opacity value of clear eggs candled via the other optical channels.

4. The apparatus of claim 2, wherein the processor is configured to detect a drop in frequency of occurrence of clear eggs.

5. The apparatus of claim 2, wherein the processor is configured to detect an increase in average light level of live eggs.

6. The apparatus of claim 2, wherein the processor is configured to detect a reduction in light levels relative to historical light levels.

7. An apparatus for candling eggs, comprising:
    a plurality of pairs of light sources and light detectors in spaced apart relationship such that eggs may pass therebetween, wherein each light source is configured to illuminate an egg with light from one or more selected portions of the spectrum, wherein each light detector is configured to receive light passing through an egg and to generate an output signal that corresponds to light received at the light detector for the egg, and wherein each light source/light detector pair defines a respective optical channel; and
    a processor in communication with each optical channel that analyzes the output signals of each optical channel to determine whether an optical path between a light source and respective light detector has been altered by debris and or by a malfunctioning light source or detector, wherein the processor is configured to perform one or more of the following:
    detect whether an average opacity value of clear eggs candled via an optical channel has dropped below an average opacity value of clear eggs candled via the other optical channels;
    detect a drop in frequency of occurrence of clear eggs;
    detect an increase in average light level of live eggs in an optical channel relative to historical values for that channel;
    detect an increase in average light level of live eggs in an optical channel relative to historical values for other optical channels; or
    detect a reduction in light levels received at a light detector in an optical channel relative to historical light levels for the optical channel; and
    wherein said apparatus further comprises a wiper operatively controlled by the processor and that is configured to wipe a surface of the light source and/or light detector.

8. The apparatus of claim 7, further comprising a cleaning fluid application system operatively controlled by the processor, and that is configured to spray a surface of the light source and/or light detector with a cleaning fluid.

* * * * *